United States Patent
Shen et al.

(10) Patent No.: US 11,471,359 B2
(45) Date of Patent: Oct. 18, 2022

(54) SYSTEM AND METHOD FOR ANKLE REHABILITATION

(71) Applicant: City University of Hong Kong, Kowloon (HK)

(72) Inventors: Yajing Shen, Kowloon (HK); Haojian Lu, Kowloon Tong (HK)

(73) Assignee: City University of Hong Kong, Kowloon (HK)

( * ) Notice: Subject to any disclaimer, the term of this patent is extended or adjusted under 35 U.S.C. 154(b) by 583 days.

(21) Appl. No.: 15/653,912

(22) Filed: Jul. 19, 2017

(65) Prior Publication Data
US 2019/0021931 A1    Jan. 24, 2019

(51) Int. Cl.
*A61H 1/02*  (2006.01)
*A63B 23/08* (2006.01)
(Continued)

(52) U.S. Cl.
CPC ......... *A61H 1/0266* (2013.01); *A61B 5/1036* (2013.01); *A61B 5/1121* (2013.01); *A61B 5/389* (2021.01); *A61B 5/6829* (2013.01); *A63B 21/0058* (2013.01); *A63B 21/00178* (2013.01); *A63B 21/00181* (2013.01); *A63B 23/08* (2013.01); *A63B 24/00* (2013.01); *A63B 24/0006* (2013.01); *A63B 24/0087* (2013.01); *G16H 20/30* (2018.01); *A61B 2505/09* (2013.01); *A61H 2201/501* (2013.01); *A61H 2201/5061* (2013.01); *A61H 2201/5064* (2013.01); *A61H 2230/605* (2013.01);
(Continued)

(58) Field of Classification Search
CPC ............... A61H 1/0266; A61H 1/0237; A61H 2201/164; A61H 2201/1642; A61H 2201/5061; A61H 2201/5064; A61H 2205/12; A61B 5/0488; A61B 5/1036; A63B 23/08; A63B 24/00; A63B 2022/0092
See application file for complete search history.

(56) References Cited

U.S. PATENT DOCUMENTS

| 4,605,220 A | * | 8/1986 | Troxel | A63B 23/08 482/112 |
| 5,148,800 A | * | 9/1992 | Pecheux | A61H 1/0237 482/79 |

(Continued)

OTHER PUBLICATIONS

Bekey, G. A.; Chi-Wu Chang; Perry, J.; Hoffer, M.;"Pattern recognition of multiple EMG signals applied to the description of human gait" (May 1977) Proceedings of the IEEE 65.5: 674-81. (Year: 1977).*

*Primary Examiner* — Valerie L Woodward
(74) *Attorney, Agent, or Firm* — Renner Kenner Law Firm; Mark L. Weber

(57) ABSTRACT

A system for ankle rehabilitation includes a motorized platform arranged to hold an ankle of a subject to be rehabilitated; a first sensor module arranged to detect signals representing movement intention of the ankle on the motorized platform; a second sensor module arranged to detect signals representing actual movement of the ankle on the motorized platform; and a processor arranged to process the signals detected by the first sensor module and the signals detected by the second sensor module, for control of movement of the motorized platform.

25 Claims, 5 Drawing Sheets

(51) Int. Cl.
*A61B 5/103* (2006.01)
*A63B 24/00* (2006.01)
*A61B 5/00* (2006.01)
*G16H 20/30* (2018.01)
*A61B 5/11* (2006.01)
*A63B 21/005* (2006.01)
*A63B 21/00* (2006.01)
*A61B 5/389* (2021.01)
*A63B 22/00* (2006.01)
*A63B 71/06* (2006.01)

(52) U.S. Cl.
CPC ............ *A63B 2022/0092* (2013.01); *A63B 2022/0094* (2013.01); *A63B 2024/0009* (2013.01); *A63B 2024/0093* (2013.01); *A63B 2071/068* (2013.01); *A63B 2071/0677* (2013.01); *A63B 2220/16* (2013.01); *A63B 2220/40* (2013.01); *A63B 2220/54* (2013.01); *A63B 2220/805* (2013.01); *A63B 2225/20* (2013.01); *A63B 2225/50* (2013.01); *A63B 2230/605* (2013.01)

(56) References Cited

U.S. PATENT DOCUMENTS

| | | | |
|---|---|---|---|
| 6,162,189 A * | 12/2000 | Girone | A61B 5/1036 600/592 |
| 2006/0069336 A1* | 3/2006 | Krebs | A61H 3/00 602/28 |
| 2011/0264238 A1* | 10/2011 | van der Merwe | A61F 2/585 623/24 |
| 2016/0058647 A1* | 3/2016 | Maddry | A61H 1/0281 623/26 |
| 2017/0027735 A1* | 2/2017 | Walsh | A61F 5/0123 |
| 2017/0258359 A1* | 9/2017 | Inoue | A61B 5/6828 |
| 2018/0064599 A1* | 3/2018 | Kato | B25J 9/0006 |

\* cited by examiner

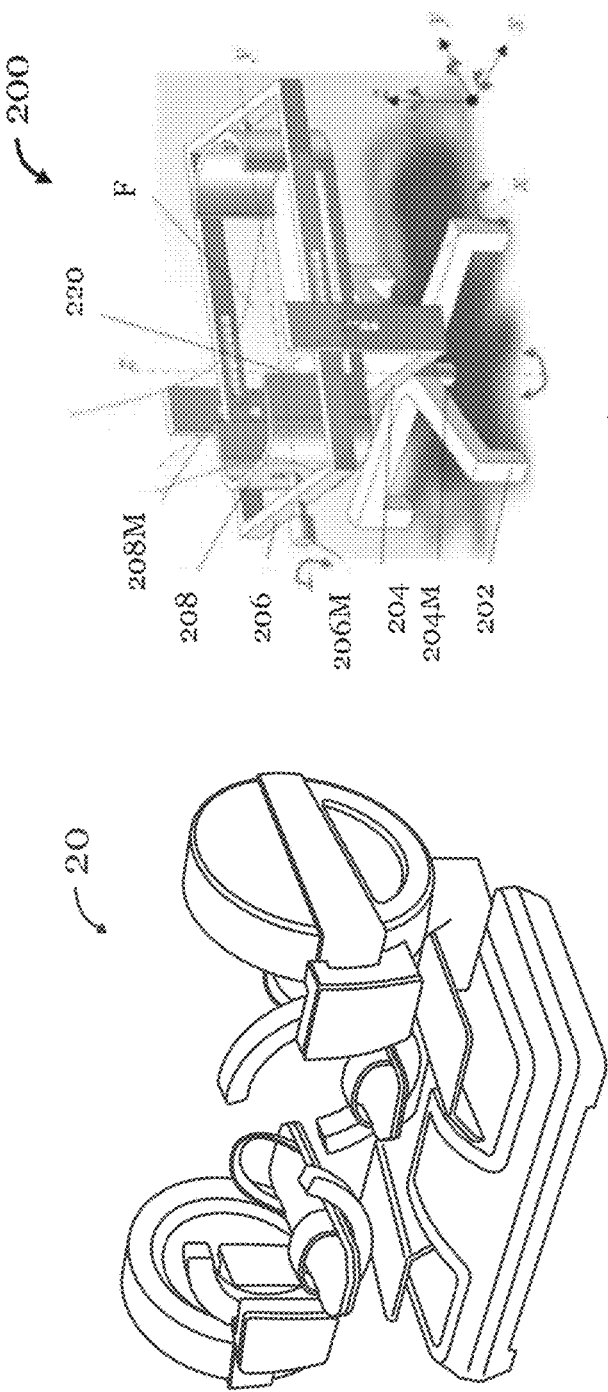
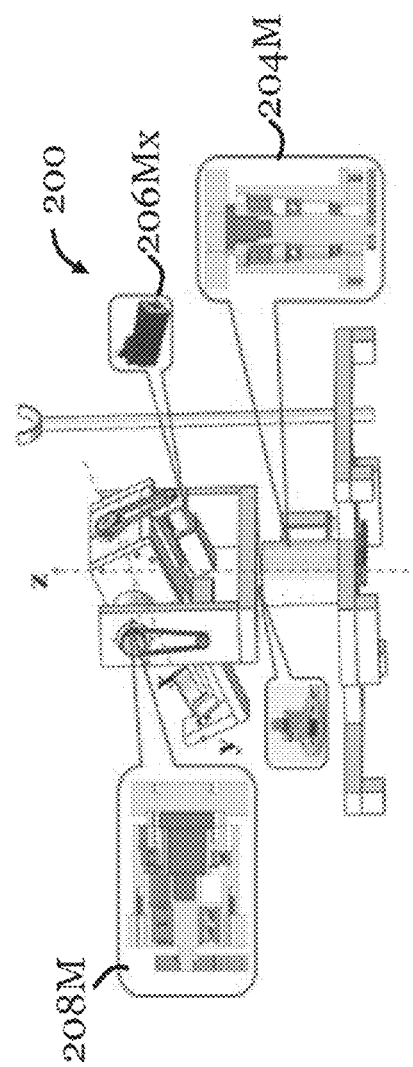
Figure 2A
Figure 2B
Figure 2C

SYSTEM AND METHOD FOR ANKLE REHABILITATION

TECHNICAL FIELD

This invention relates to a system for ankle rehabilitation and particularly, although not exclusively, to an active, robotic ankle rehabilitation and training system.

BACKGROUND

Rehabilitation plays an important role in treatment of post-stroke patients who suffer from hemiplegia. If the brain tissues of the patient are damaged but not completely destroyed, the brain tissues may gradually recover their function after months or years. In these cases, rehabilitation can speed the recovery and make the recovery more complete. Alternatively if the brain tissues are completely damaged or destroyed, other parts of the brain may sometimes learn to perform some of the functions of the destroyed tissues. In these cases, rehabilitation can assist the learning process.

The ankle joint is a hinged synovial joint located in the lower limb, and it allows up-and-down and sideways movement of the foot. Post-stroke patients, because of their weakened ankle and toe muscles (dorsiflexors), usually suffer from foot drop, valgus foot, or varus foot. In some cases, the patient tends to walk with an exaggerated flexion of the hip and knee to prevent the toes from catching on the ground during swing phase. Thus, training of the ankle joint is essential in hemiparesis rehabilitation, to enable the patient to walk properly once again.

In traditional ankle rehabilitation, a physiotherapist usually holds and moves the foot of the patient to train the ankle joint. The training may be performed 3 to 4 times a day, and it may last for several months. This method, while effective, is labor intensive and sometimes inefficient.

Another traditional ankle rehabilitation method is for the training to be performed by the patients themselves, for example, via some simple tools (such as a belt). This method reliefs the burden on the physiotherapist, but because of the patients' lack of knowledge about the rehabilitation and their tendency to avoid using impaired limb during training, results in low rehabilitation effectiveness.

Thus, there is a need to provide improved system and method for ankle rehabilitation, in particular active ankle rehabilitation system and method that are simple to operate, effective, and put little burden on the physiotherapist.

SUMMARY OF THE INVENTION

In accordance with a first aspect of the present invention, there is provided a system for ankle rehabilitation, comprising: a motorized platform arranged to hold an ankle to be rehabilitated of a subject; a first sensor module arranged to detect signals representing movement intention of the ankle on the motorized platform; a second sensor module arranged to detect signals representing actual movement of the ankle on the motorized platform; and a processor arranged to process the signals detected by the first sensor module and the signals detected by the second sensor module, for control of movement of the motorized platform.

Preferably, the motorized platform has three rotational degrees of freedom. In one embodiment, the motorized platform is rotatable independently about three mutually perpendicular axes.

Preferably, the motorized platform has six degrees of freedom, being able to translate and rotate.

Preferably, the motorized platform is adjustable such that an ankle joint of the ankle on the motorized platform can be aligned with a rotation center of the motorized platform.

Preferably, the signals representing movement intention comprises EMG signals from one or more muscle on a leg associated with the ankle on the motorized platform. The muscle may be *Fibularis longus*, tibialis anterior, *Fibularis brevis* or soleus.

Preferably, the first sensor module comprises at least one EMG sensor arranged to detect an EMG signal of a muscle on a leg on the side of the ankle on the motorized platform. The EMG sensor may be placed on the shank.

Preferably, the first sensor module comprises four EMG sensors each arranged to detect an EMG signal of respective muscles on a leg on the side of the ankle on the motorized platform. The four EMG sensors may be arranged to detect muscle signals from *Fibularis longus*, tibialis anterior, *Fibularis brevis*, and soleus respectively.

Preferably, the EMG sensors are wireless sensors. In a preferred embodiment, the EMG sensors may be Bluetooth EMG sensors operable to communication data or signal using Bluetooth communication links.

Preferably, the processor is arranged to process the signals detected by the first sensor module based on a predetermined model that represents a relationship between the signals detected and ankle movement. The relationship may be obtained from a healthy ankle of the subject.

Preferably, the second sensor module comprises: torque sensors for detecting torque applied to the ankle on the motorized platform; and position sensors for detecting position of ankle on the motorized platform.

Preferably, the motorized platform has three rotational degrees of freedom, in three mutually perpendicular axes, each of the three mutually perpendicular axes is arranged with a torque sensor and a position sensor.

Preferably, the second sensor module comprises or further comprises IMU sensors for detecting relative movement between a foot and a shank on the side of the ankle on the motorized platform.

Preferably, the second sensor module comprises or further comprises one or more accelerometers, gyroscopes, and magnetometer.

Preferably, the system further comprises a further motorized platform arranged to hold another ankle of the subject.

Preferably, the further motorized platform has three rotational degrees of freedom. In one embodiment, the further motorized platform is rotatable independently about three mutually perpendicular axes.

Preferably, the further motorized platform has six degrees of freedom.

Preferably, the further motorized platform may be physically connected with the motorized platform, or they may be separate platforms that are not physically connected with each other.

Preferably, the further motorized platform is adjustable such that an ankle joint of the other ankle on the further motorized platform can be aligned with a rotation center of the further motorized platform.

Preferably, the first sensor module comprises at least one EMG sensor arranged to detect an EMG signal of a muscle on a leg on the side of the other ankle on the further motorized platform. The muscle may be *Fibularis longus*, tibialis anterior, *Fibularis brevis*, or soleus.

Preferably, the first sensor module further comprises four EMG sensors each arranged to detect an EMG signal of respective muscles on a leg on the side of the other ankle on the further motorized platform. The four EMG sensors may be arranged to detect muscle signals from *Fibularis longus*, tibialis anterior, *Fibularis brevis*, and soleus respectively.

Preferably, the processor is further arranged to build a model that represents relationship between the signals detected and ankle movement based on the signals obtained from the first and second sensor modules for the other ankle on the further motorized platform.

Preferably, the second sensor module is further arranged to detect signals representing actual movement of the other ankle on the further motorized platform.

Preferably, the second sensor module further comprises: torque sensors for detecting torque applied to the other ankle on the further motorized platform; and position sensors for detecting position of the other ankle on the further motorized platform.

Preferably, the further motorized platform has three rotational degrees of freedom, in three mutually perpendicular axes, each of the axes being arranged with a torque sensor and a position sensor.

Preferably, the second sensor module comprises or further comprises IMU sensors for detecting relative movement between a foot and a shank on the side of the other ankle on the further motorized platform.

In accordance with a second aspect of the invention there is provided a method for ankle rehabilitation using a system, comprising: detecting first signals representing movement intention of a subject's ankle to be rehabilitated on a motorized platform; detecting second signals representing actual movement of the ankle on the motorized platform; and processing the first signals and the second signals for generation of control signals for control of movement of the motorized platform.

Preferably, the motorized platform has three rotational degrees of freedom.

Preferably, the step of processing comprises: processing the first signals based on a predetermined model that represents a relationship between the signals detected and ankle movement for the subject.

Preferably, the relationship is obtained from a healthy ankle of the subject.

Preferably, the method further comprises: detecting third signals representing movement intention of the subject's healthy ankle on a further motorized platform; detecting fourth signals representing actual movement of the ankle on the further motorized platform; and building a model representing relationship between the signals detected and ankle movement for the subject based on the third signals and the fourth signals.

Preferably, the method further comprises: controlling movement of the motorized platform based on the control signals.

In accordance with a third aspect of the invention there is provided a system for ankle rehabilitation, comprising: a first motorized platform arranged to hold an ankle to be rehabilitated of a subject; a second motorized platform arranged to hold another ankle of the subject; a first sensor module arranged to detect signals representing movement intention of the ankle on the first motorized platform, and detect signals representing movement intention of the ankle on the second motorized platform; a second sensor module arranged to detect signals representing actual movement of the ankle on the first motorized platform, and detect signals representing actual movement of the ankle on the second motorized platform; a processor arranged to process the signals detected by the first sensor module and the signals detected by the second sensor module, for control of movement of the first motorized platform.

It is an object of the present invention to address the above needs, to overcome or substantially ameliorate the above disadvantages or, more generally, to provide an improved system and method for ankle rehabilitation.

BRIEF DESCRIPTION OF THE DRAWINGS

Embodiments of the present invention will now be described, by way of example, with reference to the accompanying drawings in which:

FIG. 2A is a perspective view of an apparatus with two platforms of the system in one embodiment of the present invention;

FIG. 2B is a perspective view of a platform of the system in another embodiment of the present invention;

FIG. 2C is a perspective view of a platform of the system in yet another embodiment of the present invention;

DETAILED DESCRIPTION OF THE PREFERRED EMBODIMENT

Figure 1:
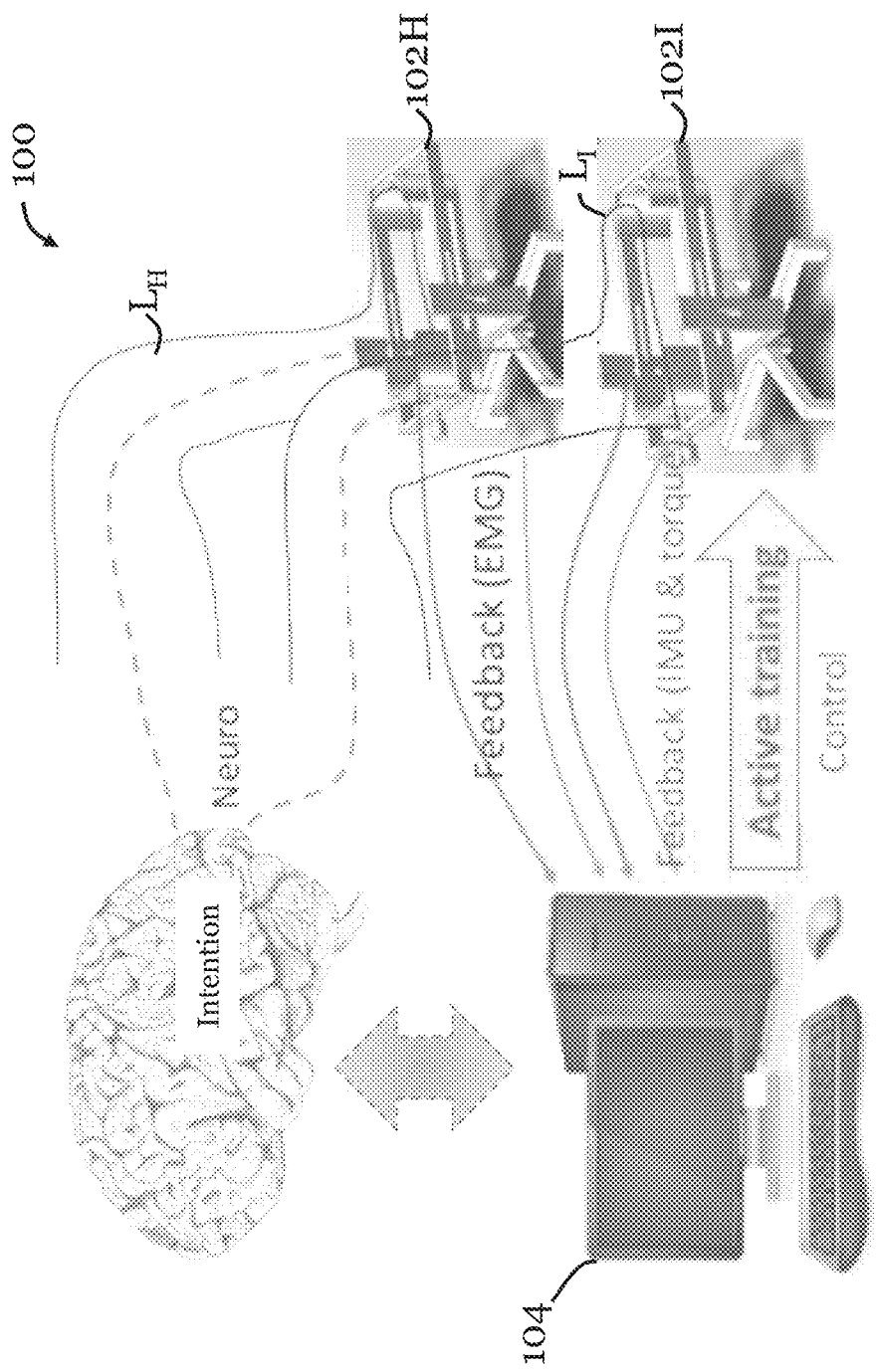
FIG. 1 is a schematic diagram of a system for ankle rehabilitation in one embodiment of the present invention.

Referring to FIG. 1, there is an ankle rehabilitation system 100 in one embodiment of the present invention. The system 100 includes a first platform 102I arranged to receive a foot with an ankle for rehabilitation, and a second platform 102H arranged to receive a foot with a healthy ankle, of the same subject (or patient). The system 100 also includes an information handling system 104, in the form of a desktop computer, arranged to obtain feedback signals from both the first platform 102I and the second platform 102H. The feedback signals may include EMG signals from the legs $L_H$, $L_I$, and IMU and torque signals associated with the respective platforms 102I, 102H. The information handling system 104 is arranged to provide control signals to control movement of the first platform 102I and the second platform 102H based on the feedback signals. The control signals allows an active training to be provided to the subject whose feet are held or placed on the platforms 102I, 102H. FIG. 1 also shows, schematically, a neuro-pathway (dotted lines) from the ankle to the brain. In this embodiment, the feedback EMG signals represent a measure of signals in this neuro-pathway to represent an intention of the subject to move the legs, especially the leg with the damaged ankle.

FIG. 2A shows an apparatus 20 with two platforms of the system in one embodiment of the present invention. As shown, in this example, the two platforms, for the two feet of the subject, are integrated in the same apparatus 20.

FIG. 2B shows a platform 200 of the system in one embodiment of the present invention. The platform 200 may be the same as those 102H, 102I illustrated in FIG. 1. The platform 200 includes a base 202, a first frame member 204 rotatable about a vertical axis Z, a second frame member 206 rotatable about a first horizontal axis X, and a third frame member 208 rotatable about a second horizontal axis Y perpendicular to the first horizontal axis X. The first frame member 204 is substantially U-shaped, and it is mounted to the base 202. The first frame member 204 includes two generally parallel arms, each arranged with an elongate slot. The second frame member 206 is substantially rectangular, with two long sides and two short sides. An elongate recess is formed on each of the long side; an opening is formed on each of the short sides. A fastener or shaft is arranged to extend through the elongate slot of the first frame member 204 and the corresponding elongate recess of the second frame member 206, to rotatably connect the first and second frame members 204, 206. The third frame member 208 includes a platform and two arcuate covers extending perpendicularly at two ends of the platform, for defining a space for receiving the foot of the subject. An elongate slot is formed on each of the two arcuate covers. A fastener or shaft fastener is arranged to extend through the opening on the short side of the second frame member 206 and the corresponding elongate slot on the arcuate cover of the third frame member 208, to rotatably connect the second and third frame members 206, 208. The second frame member 206 and the third frame member 208 are translatable with respect to the base 202. As shown in FIGS. 2B and 2C, one motor 204M, 206M, 208M, optionally with gear reducer, may be provided for each rotation axis (the vertical axis Z, the first horizontal axis X, and the second horizontal axis Y), to control the rotation movement of each of the axes. Preferably, the motors 204M, 206M, 208M operate independently such that axes may be driven independently.

By providing a platform 200 with rotatable and translatable frame members 204, 206, 208, the ankle joint 220 of the subject, with his foot placed on the platform, can be aligned to the rotational center of the platform by adjusting the frames 204, 206, 208. This is advantageous for moving the ankle joint flexibly according to its physiologically natural condition.

In one embodiment, the first frame member 204 may have a rotational range of 30°; the second frame member 206 may have a rotational range of 50°; the third frame member 208 may have a rotational range of 65°. In a preferred embodiment, the first frame member 204 may have a rotational range from −10° to 20°; the second frame member 206 may have a rotational range from −20° to 30°; the third frame member 208 may have a rotational range of −25° to 40°. These ranges correspond to the natural rotational degrees of freedom of the human ankle joint. In other embodiments, the three frame members 204, 206, 208 may have a rotational range that is smaller or larger than provided.

Although not shown in FIGS. 2B and 2C, the platform 200 as described is preferably used in pairs. The motors 204M, 206M, 208M for driving movement of the frame members 204, 206, 208 may be connected together in a control circuit, and may be controlled by an information handling system 104 or 600, such as that in FIG. 1 or 6.

To assist the subject to realize a certain movement, e.g., of the ankle, the movement intention of the subject has to be detected. In the system of the present invention, a sensor module is required to obtain signals representing movement intention of the ankle. In one embodiment, the sensor module includes at least one EMG sensor arranged on the shank of the subject for detection of EMG signals generated at the shank. In a preferred embodiment, four EMG sensors 302, 304, 306, 308 are used, each arranged to detect EMG signals from a respective one of the four main muscles—*Fibularis longus*, tibialis anterior, *Fibularis brevis*, and soleus—that regulate motion of the ankle joint of the leg. In one example, the EMG sensor may be wireless EMG sensors such as Bluetooth EMG sensors.

In a preferred embodiment, the relationship between the ankle movement and the EMG signals may be first obtained, e.g., by measuring the EMG signal of the healthy side, to build a model between the EMG signal and the ankle movement. This model may be stored in the information handling system, and used for analyzing signals picked up from the side that needs rehabilitation. As the movement on two (healthy and injured) sides of the same subject is similar, the developed model may be used to identify the movement intention of subject, and hence to control the platform to help the subject to realize such intended movement.

To realize effective training, signals representing actual movement of the ankle on the platform may be detected. In particular, the motion process, including the torque applied on the ankle joint and the movement trajectory of the foot, has to be controlled precisely. In the system of the present embodiment, a torque sensor and a position sensor (not shown) may be arranged at each rotation axis of the platform, such as that of FIG. 2B, by which the torque applied on the ankle and the position of the ankle can be measured. The position sensor may be an encoder. Preferably, in the system, torque, position, rotation range, and motion associate with the healthy side (ankle) are also taken as reference to control the injured side.

Figure 4:
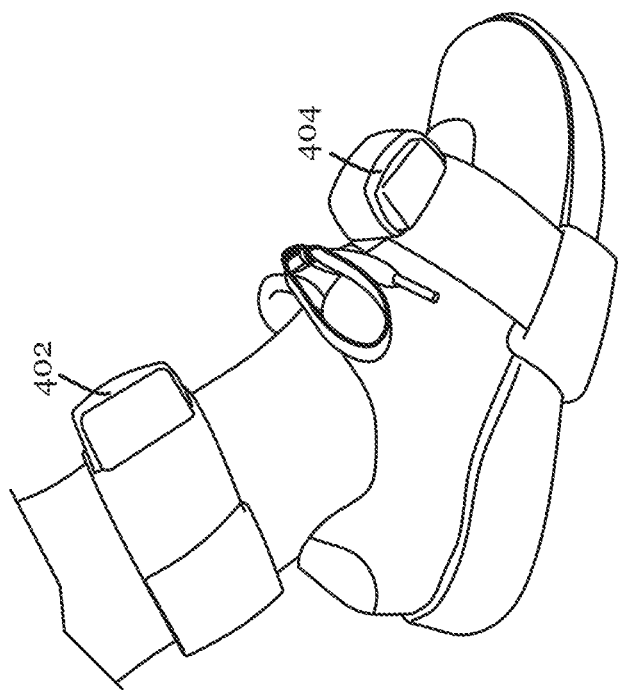
FIG. 4 is a picture showing placement of IMU sensors on the leg in one embodiment of the present invention.
Figure 3:
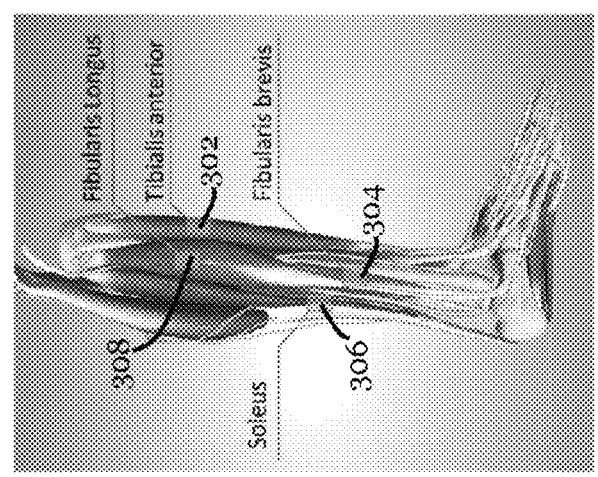
FIG. 3 is a schematic diagram illustrating placement of EMG sensors on the leg in one embodiment of the present invention.

For improved detection of dynamic movement of the subject's ankle, the system in some embodiments may comprise or further comprise an IMU sensing system. The IMU sensing system may include two Bluetooth IMU sensors, one 404 arranged on the foot (below the ankle) and another one 402 arranged on shank (above the ankle), as shown in FIG. 4. By calculating the relative movement of these two sensors, the motion of ankle joint in 3D space can be monitored dynamically.

By precisely detection both the torque and motion of the disable side, suitable torque can be generated to assist the patient to move; and the motion range of ankle joint can be monitored and controlled, thereby facilitating active training.

Figure 5A:
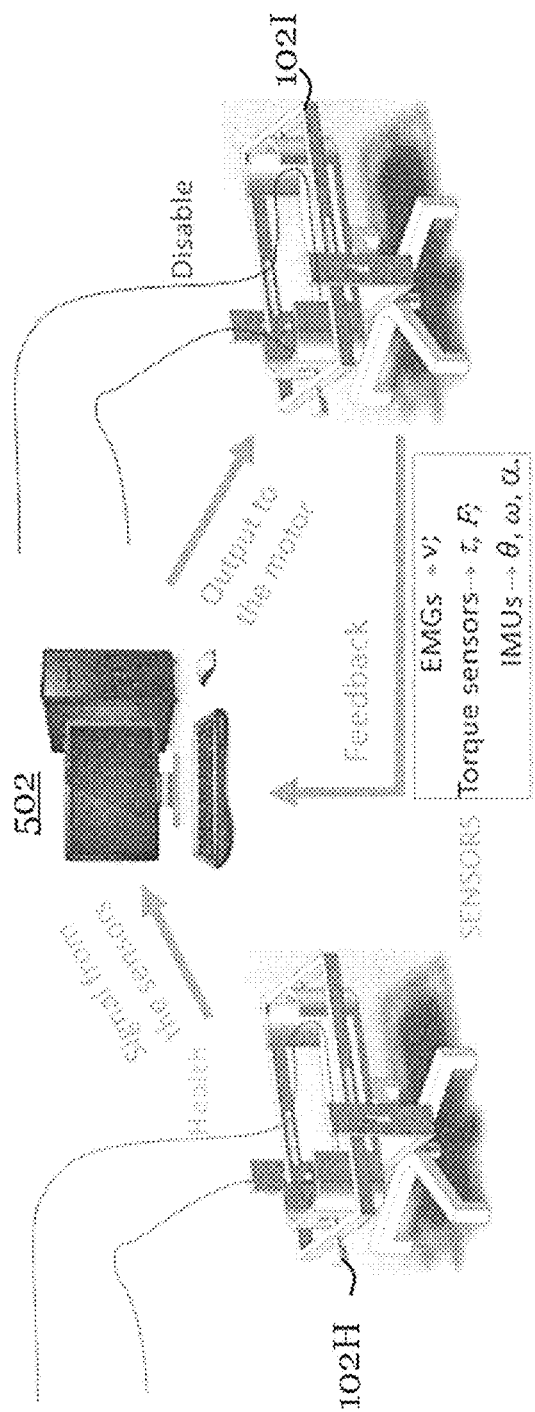
FIG. 5A is a schematic diagram illustrating operation of the system in one embodiment of the present invention.
Figure 5B:
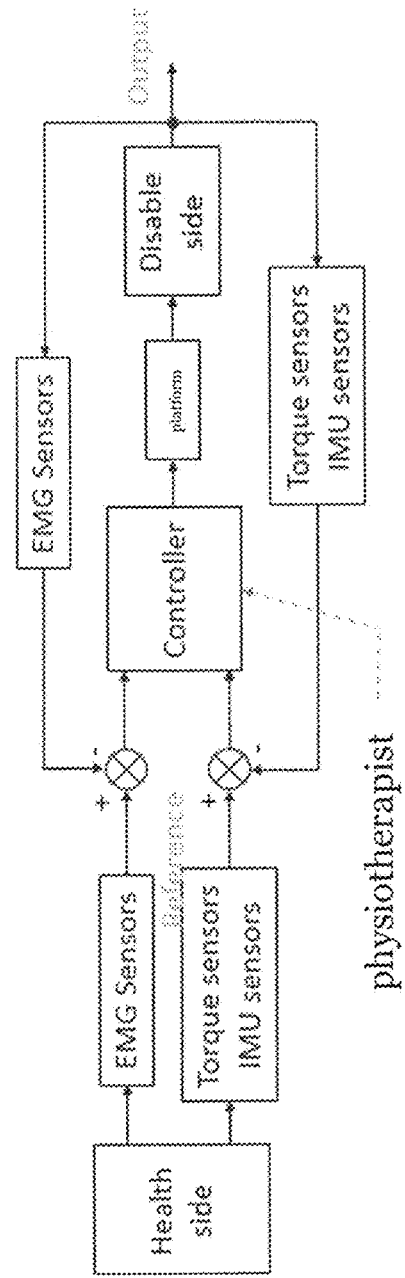
FIG. 5B is a block diagram illustrating control of operation of the system of FIG. 5A.

FIGS. 5A and 5B illustrate control operation of the ankle rehabilitation system in one embodiment of the present invention. As shown in FIG. 5A, signals obtained from the subject's foot and from the platform 102H on the healthy side are transmitted to the information handling system 502. These signals may include EMG signals measured at the shank on the healthy side, and dynamic motion and torque signals measured at the healthy side. In one embodiment, the measured EMG signals, and the measured dynamic motion and torque signals are used in the system 502 for creation of a model that represents a relationship between the signals detected and ankle movement, for control of the injured side. In FIG. 5A, the information handling system 502 is also arranged to obtain feedback from the subject's foot and from the platform 102I on the injured side (the side with ankle to be or being rehabilitated). These signals may include EMG signals measured at the shank on the injured side, and dynamic motion and torque signals measured at the injured side. The information handling system 502 is arranged to provide control signals to the platform 102I of the injured side, for active, real-time, automatic control of movement of the platform 102I.

As shown in FIG. 5B, signals are provided from the healthy side to the controller through the EMG sensor and the torque and IMU sensors. Signals are also provided from the injured side to the controller through the EMG sensor and the torque and IMU sensors. The controller receives and processes these signals from the healthy side and the injured side, in particular processes the signals from the injured side based on the predetermined model, to provide control signals to actively control operation of the platform of the injured side, for example, by controlling operation of the motors associated with the platform. In one embodiment, the information handling system may store the signals obtained at the health side or at the injured side, or at both sides, for record keeping and subsequent analysis.

Figure 6:
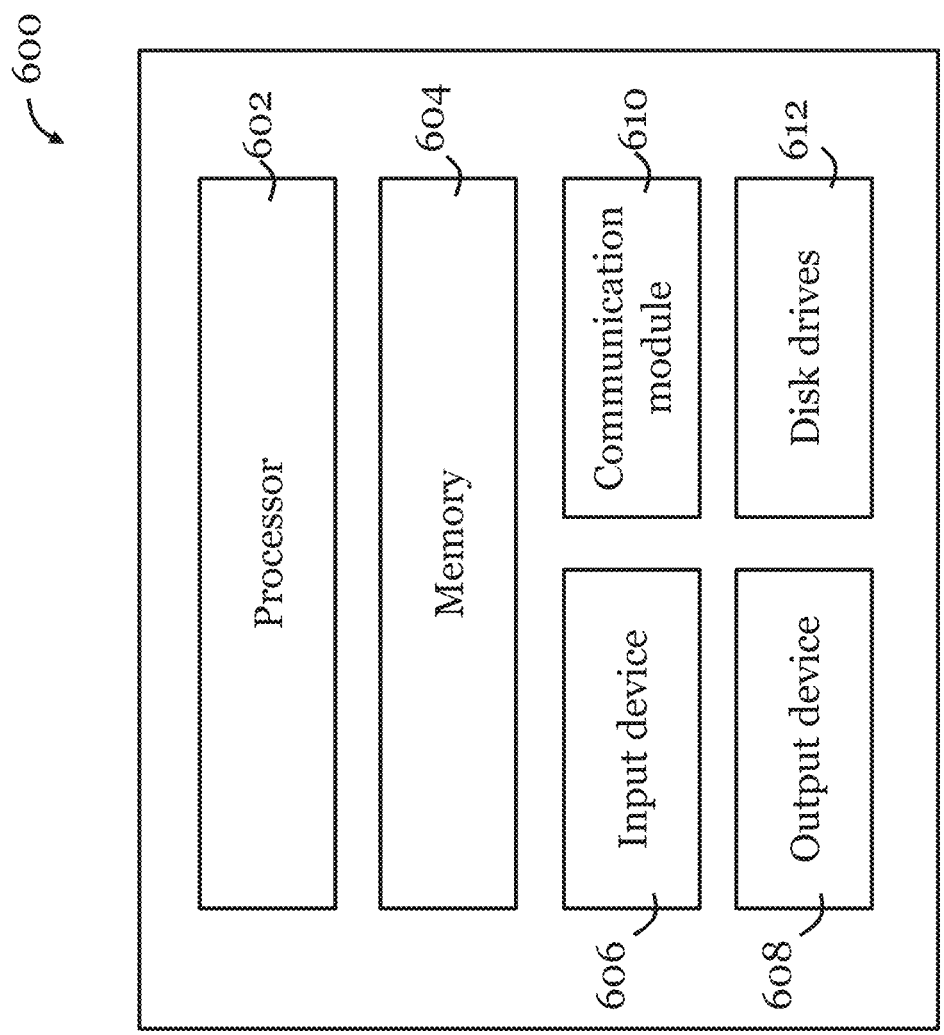
FIG. 6 is a block diagram of an information handling system arranged to implement the operation method in FIGS. 5A and 5B.

Referring to FIG. 6, there is shown a schematic diagram of an exemplary information handling system 600that can be used as for implementing the method of the present invention. The information handling system 600 may take different form, for example, the form of a desktop computer (like 104 in FIG. 1, 502 in FIG. 5A), a notebook, a server, a tablet, a smart phone, etc. Preferably, the information handling system 600 may have different configurations, and it generally comprises suitable components necessary to receive, store and execute appropriate computer instructions or codes. The main components of the information handling system 600are a processing unit 602 and a memory unit 604. The processing unit 602 is a processor such as a CPU, an MCU, etc. The memory unit 604 may include a volatile memory unit (such as RAM), a non-volatile unit (such as ROM, EPROM, EEPROM and flash memory) or both. Preferably, the information handling system 600 further includes one or more input devices 606 such as a keyboard, a mouse, a stylus, a microphone, a tactile input device (e.g., touch sensitive screen) and a video input device (e.g., camera). The information handling system 600 may further include one or more output devices 608 such as one or more displays, speakers, disk drives, and printers. The displays may be a liquid crystal display, a light emitting display or any other suitable display that may or may not be touch sensitive. The information handling system 600 may further include one or more disk drives 612 which may encompass solid state drives, hard disk drives, optical drives and/or magnetic tape drives. A suitable operating system may be installed in the information handling system 600, e.g., on the disk drive 612 or in the memory unit 604 of the information handling system 600. The memory unit 604 and the disk drive 612 may be operated by the processing unit 602. The information handling system 600 also preferably includes a communication module 610 for establishing one or more communication links (not shown) with one or more other computing devices such as a server, personal computers, terminals, wireless or handheld computing devices. The communication module 610 may be a modem, a Network Interface Card (NIC), an integrated network interface, a radio frequency transceiver, an optical port, an infrared port, a USB connection, or other interfaces. The communication links may be wired or wireless for communicating commands, instructions, information and/or data. Preferably, the processing unit 602, the memory unit 604, and optionally the input devices 606, the output devices 608, the communication module 610 and the disk drives 612 are connected with each other through a bus, a Peripheral Component Interconnect (PCI) such as PCI Express, a Universal Serial Bus (USB), and/or an optical bus structure. In one embodiment, some of these components may be connected through a network such as the Internet or a cloud computing network.

The above embodiments of the present invention have provided an ankle rehabilitation system that makes use of the conscious movement choice, i.e., the intended movement, of the subject, for active training. The system includes a platform that can simulate natural foot movement by virtue of its movement freedom. The system uses hybrid sensing means, EMG sensing and dynamic position, force, and/or motion sensing, for active rehabilitation control, which improves rehabilitation efficiency and effectiveness.

Although not required, the embodiments described with reference to the Figures can be implemented as an application programming interface (API) or as a series of libraries for use by a developer or can be included within another software application, such as a terminal or personal computer operating system or a portable computing device operating system. Generally, as program modules include routines, programs, objects, components and data files assisting in the performance of particular functions, the skilled person will understand that the functionality of the software application may be distributed across a number of routines, objects or components to achieve the same functionality desired herein.

It will also be appreciated that where the methods and systems of the present invention are either wholly implemented by computing system or partly implemented by computing systems then any appropriate computing system architecture may be utilized. This will include stand-alone computers, network computers and dedicated hardware devices. Where the terms "computing system" and "computing device" are used, these terms are intended to cover any appropriate arrangement of computer hardware capable of implementing the function described.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

Any reference to prior art contained herein is not to be taken as an admission that the information is common general knowledge, unless otherwise indicated.

The invention claimed is:

1. A system for ankle rehabilitation, comprising:
a motorized platform arranged to hold a subject's ankle to be rehabilitated, the motorized platform comprising:
a base;
a first frame member rotatable about a vertical axis;
a second frame member rotatable about a first horizontal axis and translatable with respect to the base;
a third frame member rotatable about a second horizontal axis perpendicular to the first horizontal axis and translatable with respect to the base;
a first motor arranged to control rotation movement of the first frame member about the vertical axis;
a second motor arranged to control rotation movement of the second frame member about the first horizontal axis; and
a third motor arranged to control rotation movement of the third frame member about the second horizontal axis;
the first, second, and third frame members being adjustable to align an ankle joint of a subject's ankle to be rehabilitated with a rotation center of the motorized platform for moving the ankle joint flexibly according to its physiologically natural condition;
a first sensor module arranged to detect signals representing movement intention of the ankle to be rehabilitated on the motorized platform;
a second sensor module arranged to detect signals representing actual movement of the ankle to be rehabilitated on the motorized platform;

a processor arranged to process the signals detected by the first sensor module and the signals detected by the second sensor module and to operate the first, second, and third motors independently to control movement of the motorized platform to assist the subject in realizing the intended movement using the ankle to be rehabilitated; and a memory storing a predetermined model that represents a relationship between signals representing movement intention of a healthy ankle of the subject and the corresponding actual movement of the healthy ankle;

wherein the processor is arranged to process the signals detected by the first and second sensor modules based on the predetermined model and, based on the processing, control movement of the motorized platform so as to assist the subject in realizing the intended movement of the ankle to be rehabilitated.

2. The system of claim 1, wherein the motorized platform has six degrees of freedom.

3. The system of claim 1, wherein the signals representing movement intention comprise EMG signals from one or more muscles on a leg associated with the ankle to be rehabilitated on the motorized platform.

4. The system of claim 1, wherein the first sensor module comprises at least one EMG sensor arranged to detect an EMG signal of a muscle on a leg on the side of the ankle to be rehabilitated on the motorized platform.

5. The system of claim 4, wherein the first sensor module comprises four EMG sensors each arranged to detect an EMG signal of respective muscles on a leg on the side of the ankle to be rehabilitated on the motorized platform, the respective muscles comprising *Fibularis longus*, tibialis anterior, *Fibularis brevis*, and soleus, which are arranged to regulate ankle joint motion.

6. The system of claim 1, wherein the second sensor module comprises:
torque sensors for detecting a torque applied to the ankle to be rehabilitated on the motorized platform; and
position sensors for detecting a position of the ankle to be rehabilitated on the motorized platform.

7. The system of claim 6, wherein the motorized platform has three rotational degrees of freedom, in three mutually perpendicular axes, each of the three mutually perpendicular axes is arranged with a torque sensor and a position sensor.

8. The system of claim 6, wherein the second sensor module further comprises:
IMU sensors for detecting relative movement between a foot and a shank on the side of the ankle to be rehabilitated on the motorized platform.

9. The system of claim 1, wherein the second sensor module comprises:
IMU sensors for detecting relative movement between a foot and a shank on the side of the ankle to be rehabilitated on the motorized platform.

10. The system of claim 1, further comprising:
a further motorized platform arranged to hold another ankle of the subject.

11. The system of claim 10, wherein the further motorized platform has three rotational degrees of freedom.

12. The system of claim 10, wherein the further motorized platform has six degrees of freedom.

13. The system of claim 10, wherein the further motorized platform is adjustable such that an ankle joint of the other ankle on the further motorized platform can be aligned with a rotation center of the further motorized platform.

14. The system of claim 10, wherein the processor is further arranged to build the predetermined model using the first and second sensor modules and the further motorized platform.

15. The system of claim 10, wherein the second sensor module is further arranged to detect signals representing actual movement of the other ankle on the further motorized platform.

16. The system of claim 15, wherein the second sensor module comprises:
torque sensors for detecting a torque applied to the other ankle on the further motorized platform; and
position sensors for detecting a position of the other ankle on the further motorized platform.

17. The system of claim 16, wherein the further motorized platform has three rotational degrees of freedom, in three mutually perpendicular axes, each of the axes being arranged with a torque sensor and a position sensor.

18. The system of claim 16, wherein the second sensor module further comprises:
IMU sensors for detecting relative movement between a foot and a shank on the side of the other ankle on the further motorized platform.

19. The system of claim 15, wherein the second sensor module comprises:
IMU sensors for detecting relative movement between a foot and a shank on the side of the other ankle on the further motorized platform.

20. The system of claim 10, wherein the first sensor module is further arranged to detect signals representing movement intention of the subject's other ankle on the further motorized platform.

21. The system of claim 20, wherein the first sensor module comprises at least one EMG sensor arranged to detect an EMG signal of a muscle on a leg on the side of the other ankle on the further motorized platform.

22. The system of claim 21, wherein the first sensor module comprises four EMG sensors each arranged to detect an EMG signal of respective muscles on a leg on the side of the other ankle on the further motorized platform, the respective muscles comprising *Fibularis longus*, tibialis anterior, *Fibularis brevis*, and soleus, which are arranged to regulate ankle joint motion.

23. The system of claim 1, wherein the third frame member includes a platform and two arcuate covers extending perpendicularly at two ends of the third frame member to define a space for receiving the foot of the subject on the same side as the subject's ankle to be rehabilitated.

24. A method for ankle rehabilitation, comprising:
detecting, using a first sensor module, first signals representing movement intention of a subject's ankle to be rehabilitated on a motorized platform, the motorized platform comprising: a base; a first frame member rotatable about a vertical axis; a second frame member rotatable about a first horizontal axis and translatable with respect to the base; a third frame member rotatable about a second horizontal axis perpendicular to the first horizontal axis and translatable with respect to the base; a first motor arranged to control rotation movement of the first frame member about the vertical axis; a second motor arranged to control rotation movement of the second frame member about the first horizontal axis; and a third motor arranged to control rotation movement of the third frame member about the second horizontal axis; the first, second, and third frame members being adjustable to align an ankle joint of a subject's ankle to be rehabilitated with a rotation center of the motorized platform for moving the ankle joint flexibly according to its physiologically natural condition;

detecting, using a second sensor module second signals representing actual movement of the ankle to be rehabilitated on the motorized platform; and processing, using a processor, the first signals detected by the first sensor module and the second signals detected by the second sensor module for generation of control signals for operating the first, second, and third motors independently to control of movement of the motorized platform to assist the subject in realizing the intended movement using the ankle to be rehabilitated; wherein the processing step comprises:

processing, using the processor, the first signals detected by the first sensor module and the second signals detected by the second sensor module based on a predetermined model that represents a relationship between signals representing movement intention of a healthy ankle of the subject and the corresponding actual movement of the healthy ankle; and wherein the method further comprises controlling movement of the motorized platform based on the processing so as to assist the subject in realizing the intended movement of the ankle to be rehabilitated.

25. The method of claim 24, further comprising detecting third signals representing movement intention of the subject's healthy ankle on a further motorized platform;

detecting fourth signals representing actual movement of the healthy ankle on the further motorized platform; and building the predetermined model representing a relationship between the signals detected and ankle movement for the subject based on the third signals and the fourth signals.

\* \* \* \* \*